United States Patent [19]

Leone-Bay et al.

[11] Patent Number: 4,794,189

[45] Date of Patent: Dec. 27, 1988

[54] SYNTHESIS OF N-SUCCINIMIDYL HALOACETYL AMINOBENZOATES

[75] Inventors: Andrea Leone-Bay, Ridgefield, Conn.; Peter E. Timony, Valley Cottage, N.Y.

[73] Assignee: Akzo America Inc., New York, N.Y.

[21] Appl. No.: 129,493

[22] Filed: Dec. 7, 1987

[51] Int. Cl.$^4$ .............................. C07D 207/46
[52] U.S. Cl. ........................................ 548/542
[58] Field of Search ............................ 548/542

[56] References Cited

U.S. PATENT DOCUMENTS 4,218,539 8/1980 Weltman ........................... 548/542
4,251,445 2/1981 Weltman ........................... 548/542

OTHER PUBLICATIONS

Chem. Abstracts, vol. 56, Abst. No. 4683a, Ueda, et al.

Noller Textbook of Organic Chemistry, 3rd Edition, W. B. Saunders Co., Philadelphia, 1966, p. 98.

Staros, Biochemistry, vol. 21, pp. 3950–3955, 1982.

*Primary Examiner*—Mary C. Lee
*Assistant Examiner*—Robert C. Whittenbaugh
*Attorney, Agent, or Firm*—Richard P. Fennelly; Louis A. Morris

[57] ABSTRACT

N-succinimidyl haloacetyl aminobenzoates are formed by: (a) reacting an aminobenzoic acid with haloacetylhalide to form a haloacetylaminobenzoic acid; (b) optionally converting the haloacetylaminobenzoic acid from (a) to the ultimately desired halo intermediate compound; (c) reacting the compound from (b) with oxalyl halide to form the corresponding benzoyl compound; and (d) coupling the benzoyl compound from (c) with an N-hydroxysuccinimide to form the ultimately desired N-succinimidyl haloacetyl aminobenzoate.

4 Claims, No Drawings

SYNTHESIS OF N-SUCCINIMIDYL HALOACETYL AMINOBENZOATES

BACKGROUND OF THE PRESENT INVENTION

1. Field of the Invention

The present invention relates to a novel process for the synthesis of N-succinimidyl haloacetyl aminobenzoate compounds which find utility as crosslinking agents.

2. Description of the Prior Art

N-succinimidyl haloacetyl aminobenzoate crosslinking agents are described in U.S. Pat. Nos. 4,218,539 and 4,251,445. These patents teach, for example, that such compounds can be prepared by first reacting iodoacetic anhydride and aminobenzoic acid in dioxane to form an iodoacetylaminobenzoic acid which was combined with dicyclohexyl carbodiimide and N-hydroxysuccinimide to form the desired N-succinimidyl haloacetyl aminobenzoate.

SUMMARY OF THE PRESENT INVENTION

The present invention relates to formation of N-succinimidyl haloacetyl aminobenzoate compounds by:

(a) reacting an aminobenzoic acid with haloacetylhalide to form a haloacetylaminobenzoic acid;

(b) converting the haloacetylaminobenzoic acid to the corresponding iodo acid compound; and (c) reacting the compound with oxalyl halide, forming the corresponding benzoyl compound, and coupling the benzoyl compound with an N-hydroxysuccinimide compound to form the desired N-succinimidyl haloacetyl aminobenzoate compound.

DETAILED DESCRIPTION OF THE INVENTION

The N-succinimidyl haloacetyl aminobenzoate compounds to which the present invention relates are illustrated by the types of compounds shown in U.S. Pat. Nos. 4,218,539 and 4,251,445. Included within the term "N-succinimidyl haloacetyl aminobenzoate" are those compounds in which the ring moieties are substituted with non-interfering groups to the synthesis reaction described herein. Representative examples of compounds which fall within the desired class of compound include N-succinimidyl-(4-iodoacetyl)-aminobenzoate and N-sulfosuccinimidyl-(4-iodoacetyl)-aminobenzoate. The latter compound carries a sulfo-substituent ($-SO_2ONa$) on the succinimidyl ring.

The first step in the instant process involves formation of a haloacetylaminobenzoic acid compound by reacting an aminobenzoic acid with haloacetyl halide. In a preferred embodiment, the reactant used in this step is chloroacetyl chloride. This reaction step is known (e.g., see Chemical Abstracts, Vol. 56, 4683a) from the literature and is exemplified in Example 1, below. It is advantageously conducted by gradually adding the chloroacetylchloride, with cooling, to the aminobenzoic acid, in base solution, followed by later acidification and recovery of the desired product.

The ultimately desired haloacetylaminobenzoic acid intermediate used in the present process can then be made by an appropriate halogen exchange reaction, if necessary, by stirring the haloacetylaminobenzoic acid in a saturated solution of alkali metal halide in acetone. In a preferred embodiment due to cost considerations, the iodoacetylaminobenzoic acid intermediate is formed by this step.

Once the haloacetylaminobenzoic acid compound from the preceding step is formed, it is reacted with oxalyl halide, e.g., oxalyl chloride, followed by quenching of the resulting benzoyl halide, e.g., the benzoyl chloride, with the N-hydroxysuccinimide compound (see J. V. Staros, Biochem., 1982, 21, 3950).

An exemplary reaction scheme is depicted below for the synthesis of N-sulfosuccinimidyl-(4-iodoacetyl)-aminobenzoate, also termed "sulfo-SIAB":

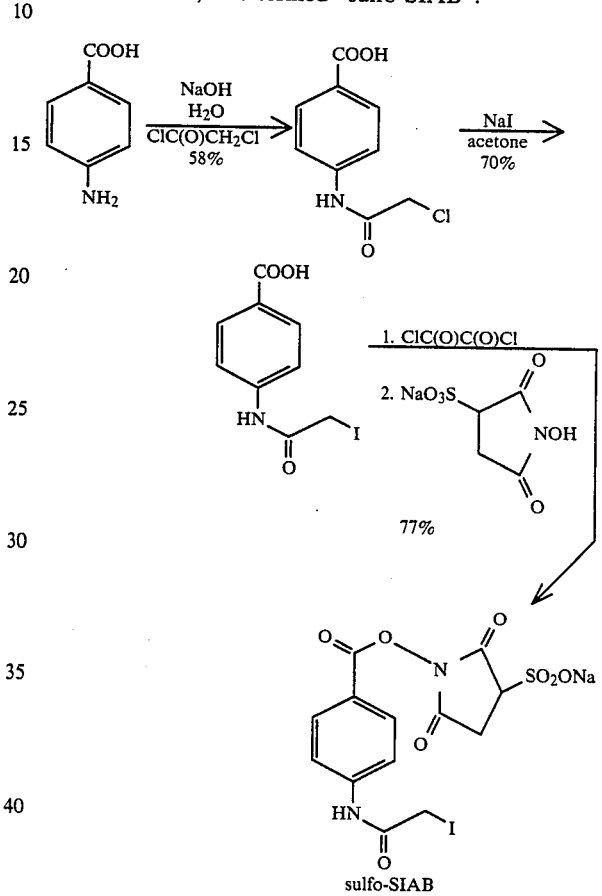

sulfo-SIAB

The present invention is further illustrated by the Examples which follow.

EXAMPLE 1

This Example illustrates the preparation of 4-iodoacetylaminobenzoic acid.

4-Chloroacetylaminobenzoic acid (10 grams, 46.7 millimoles), formed by the procedure described by T. Ueda and S. Kato in Japan Pat. No. 10,972 ('61)—abstracted in Chem. Abstr., Vol. 56, 4683a, was stirred in a saturated solution of sodium iodide/acetone (100 milliliters) for 24 hours at room temperature. The resulting yellow suspension was diluted with water (200 milliliters) and extracted twice with ethyl acetate (2×100 milliliters). The combined ethyl acetate layers were washed with brine, dried over anhydrous magnesium sulfate and concentrated in vacuo to give 4-iodoacetylaminobenzoic acid as a tan solid (10 grams, 70%). This material was used without further purification.

EXAMPLE 2

This Example illustrates the preparation of N-sulfosuccinimidyl-(4-iodoacetyl)-aminobenzoate.

Oxalyl chloride (2.9 milliliters, 32.9 millimoles) was added dropwise to a suspension of 4-iodoacetylaminobenzoic acid in benzene (20.0 milliliters) (from Example 1) at such a rate as to control the evolution of $CO_2$. After addition was complete, the mixture was stirred for 30 minutes at room temperature and for 2 hours at reflux. N-hydroxysulfosuccinimide (7.15 grams, 32.9 millimoles) was added in one portion and the reaction heated at reflux for an additional hour. Concentration in vacuo followed by trituration with ether gave the desired N-sulfosuccinimidyl-(4-iodoacetyl)aminobenzoate as a tan solid (12.9 grams, 77%).

The foregoing Examples illustrate certain preferred embodiments of the present invention and should not, therefore, be construed in a limiting sense. The scope of protection sought is set forth in the claims which follow.

We claim:

1. A process for preparing N-succinimidyl haloacetyl aminobenzoate compounds which comprises:
   (a) reacting an aminobenzoic acid with haloacetylhalide to form a haloacetylaminobenzoic acid;
   (b) optionally converting the haloacetylaminobenzoic acid to the differing and desired haloacetylaminobenzoic acid;
   (c) reacting the haloacetylaminobenzoic acid with oxalyl halide to form the corresponding benzoyl compound; and
   (d) coupling the benzoyl compound from (c) with an N-hydroxysuccinimide to form the N-succinimidyl haloacetyl aminobenzoate.

2. A process as claimed in claim 1 wherein the N-succinimidyl haloacetyl aminobenzoate is an N-sulfosuccinimidyl haloacetyl aminobenzoate.

3. A process as claimed in claim 2 wherein the N-sulfosuccinimidyl haloacetyl aminobenzoate is N-sulfosuccinimidyl iodoacetyl aminobenzoate.

4. A process as claimed in claim 3 wherein the compound is N-sulfosuccinimidyl-(4-iodoacetyl)-aminobenzoate.

* * * * *